United States Patent
Mainguet et al.

(10) Patent No.: US 10,474,864 B2
(45) Date of Patent: Nov. 12, 2019

(54) METHOD OF CAPTURING THERMAL PATTERN WITH OPTIMISED HEATING OF PIXELS

(71) Applicants: COMMISSARIAT A L'ENERGIE ATOMIQUE ET AUX ENERGIES ALTERNATIVES, Paris (FR); IDEMIA IDENTITY & SECURITY FRANCE, Issy-les-Moulineaux (FR)

(72) Inventors: Jean-Francois Mainguet, Grenoble (FR); Joel Yann Fourre, Marly le Roi (FR)

(73) Assignees: COMMISSARIAT A L'ENERGIE ATOMIQUE ET AUX ENERGIES ALTERNATIVES, Paris (FR); IDEMIA IDENTITY & SECURITY FRANCE, Issy-les-Moulineaux (FR)

( * ) Notice: Subject to any disclaimer, the term of this patent is extended or adjusted under 35 U.S.C. 154(b) by 48 days.

(21) Appl. No.: 15/662,805

(22) Filed: Jul. 28, 2017

(65) Prior Publication Data

US 2018/0032782 A1 Feb. 1, 2018

(30) Foreign Application Priority Data

Jul. 29, 2016 (FR) ...................................... 16 57390

(51) Int. Cl.
*G06K 9/00* (2006.01)
*A61B 5/1172* (2016.01)
(Continued)

(52) U.S. Cl.
CPC .......... *G06K 9/0002* (2013.01); *A61B 5/1172* (2013.01); *G01J 5/046* (2013.01); *G01J 5/34* (2013.01)

(58) Field of Classification Search
CPC .......... G06K 9/0002; G01J 5/046; G01J 5/34; A61B 5/1172
See application file for complete search history.

(56) References Cited

U.S. PATENT DOCUMENTS

| 4,394,773 A | 7/1983 | Ruell |
| 4,429,413 A | 1/1984 | Edwards |

(Continued)

FOREIGN PATENT DOCUMENTS

| EP | 0 840 250 A1 | 5/1998 |
| EP | 2 385 486 A1 | 11/2011 |

OTHER PUBLICATIONS

U.S. Appl. No. 15/662,778, filed Jul. 28, 2017, Mainguet et al.
(Continued)

*Primary Examiner* — John B Strege
(74) *Attorney, Agent, or Firm* — Oblon, McClelland, Maier & Neustadt, L.L.P.

(57) ABSTRACT

There is provided a method of capturing a thermal pattern by a sensor including a matrix of several rows and columns of pixels, and heating elements, each heating element associated with at least one pixel, and configured to heat a heat sensitive measurement element for measurement of the pixel independently of other heating elements during reading of the pixel, the method including, during a reading of at least one first pixel, the heat sensitive measurement element of the at least one first pixel is heated by a heating element associated with the at least one first pixel, and also during the reading, the heat sensitive measurement element of at least one second pixel is heated by at least one other heating element associated with the at least one second pixel, the at least one second pixel being read before or after the reading of the at least one first pixel.

14 Claims, 2 Drawing Sheets

(51) Int. Cl.
*G01J 5/04* (2006.01)
*G01J 5/34* (2006.01)

(56) References Cited

U.S. PATENT DOCUMENTS

| | | | |
|---|---|---|---|
| 4,948,963 A * | 8/1990 | Ballingall | H01L 27/14649 250/332 |
| 5,818,043 A * | 10/1998 | Buchy | G01J 5/20 250/332 |
| 6,061,464 A | 5/2000 | Leger | |
| 6,091,837 A | 7/2000 | Dinh | |
| 6,289,114 B1 | 9/2001 | Mainguet | |
| 8,801,274 B2 | 8/2014 | Mainguet et al. | |
| 2006/0050935 A1 | 3/2006 | Bustgens et al. | |
| 2007/0147608 A1* | 6/2007 | Mainguet | G06F 7/588 380/46 |
| 2011/0280276 A1 | 11/2011 | Mainguet et al. | |

OTHER PUBLICATIONS

U.S. Appl. No. 14/583,967, filed Dec. 29, 2014, Mainguet et al.
U.S. Appl. No. 15/445,235, filed Feb. 28, 2017, Mainguet et al.
U.S. Appl. No. 14/583,967, filed Dec. 29, 2014, 2015/0191309 A1, Jean-Francois Mainguet, et al.
U.S. Appl. No. 15/445,235, filed Feb. 28, 2017, Sebastien Becker, et al.
French Preliminary Search Report dated Apr. 26, 2017 in French Application 16 57390 filed on Jul. 29, 2016 (with English Translation of Categories of cited documents).
Hirofumi Miki, et al. "Survey of Biometric Authentication and Proposal of New Sensing Mechanism", International Journal of Engineering and Applied Sciences (IJEASE), vol. 3, No. 4, 2016, 10 pages.
Jean-Francois Mainguet "Fingerprint sensing techniques", Biometrics, http://fingerchip.pagesperso-orange.fr/biometrics/types/fingerprint_sensors_physics.htm, 2014, 13 pages.

* cited by examiner

METHOD OF CAPTURING THERMAL PATTERN WITH OPTIMISED HEATING OF PIXELS

TECHNICAL DOMAIN AND PRIOR ART

The invention relates to a method of capturing a thermal pattern in which heating of heat sensitive measurement elements of pixels of the sensor with which the method is implemented is optimised. This method is advantageously used to capture a fingerprint by heat detection.

A fingerprint sensor includes heat detection means. These heat detection means may consist of pyroelectric elements, diodes, thermistor or any other element sensitive to temperature to convert a temperature variation into a variation of potential or electrical current.

A fingerprint can be detected using "passive" sensors making use of a temperature difference between the finger and the sensor, as disclosed in documents U.S. Pat. No. 4,394,773, 4,429,413 and 6,289,114. However, these sensors have the disadvantage that they make a measurement that is only dependent on the temperature difference between the finger and the sensor. Therefore it is possible that a null signal can be obtained when the temperatures of the finger and the sensor are the same (for example when the finger is held on the sensor for a certain time), or the contrast of the captured images varies and then creates problems with later image processing.

"Active" fingerprint sensors have been disclosed, for example as described in documents U.S. Pat. No. 6,091,837 and EP 2 385 486 A1, to solve problems raised with passive thermal sensors, particularly in the case of a static acquisition in which the finger is kept still. Each pixel in such a sensor comprises a pyroelectric capacitor composed of two conducting electrodes between which there is a portion of pyroelectric material and a heating element. This heating element dissipates a certain quantity of heat in the pixel, and the temperature rise of the pixel is measured after a given acquisition time called the integration time, in the presence of a finger on the sensor. This makes it possible to make a distinction between the presence of a ridge or valley of the detected fingerprint at each pixel, depending on whether heat is absorbed by the skin (pixel at a ridge on the fingerprint) or remains in the pixel (pixel at a valley on the fingerprint). The result is that the final temperature in the case of a pixel in the presence of a ridge at which heat is absorbed by the skin, is lower than the case of a pixel in the presence of a valley.

To a first order of magnitude, such a sensor can measure the thermal capacity, also called the specific heat or specific heat capacity, of an element in contact with the sensor. Measurements obtained also depend on the thermal conductivity between the sensor and the part of the element (ridge or valley in the case of a fingerprint) present.

An active thermal sensor is formed by coupling the pixels of this sensor to heating elements, usually using the Joule effect that dissipate heat from a resistive element through which a current passes. One of the levels of the technological stack forming the pixels is advantageously used to form these heating elements. For example, one of the electrically conducting levels can be used to make transistors and interconnections of the sensor if one of these levels comprises a conducting material with appropriate resistivity and on which one of the voltages already available can be applied, for example a sensor power supply voltage, to generate heating using the Joule effect. This is used particularly when the sensor comprises TFT ("Thin-Film Transistors»), made on a glass or plastic substrate.

The pixels in such a sensor are made by forming a matrix composed of several rows and several columns. Pixels are usually read row by row. The heating elements can then also be controlled by row using a transistor at the end of each row, thus avoiding the addition of control transistors in each pixel. Each row of heating elements may for example be connected at the pixels matrix side to the ground, and at the other side to the control transistor associated with the pixel row and connected to a power supply adapted so as to control the current passing through the heating elements and therefore the thermal power injected into the pixels by these heating elements using the Joule effect.

The variation of the number of electrical charges appearing in the pyroelectric capacitors of the pixels in one of the pixel rows of the active thermal sensor can be read by activating the row of heating elements associated with the pixel row to be read, and circulating a heating current in this row of heating elements. Each of the pixels comprises at least one selection transistor, and the pixel selection transistors of each pixel column are connected to a conducting row, itself connected to a read circuit. When a pixel row is read, the pixel selection transistors in this row are put into the conducting state so that the active nodes of the pixels in this row can be connected to the read circuits at the bottom of each of the pixel columns. Blocked pixel selection transistors belonging to other pixel rows prevent the displacement of charges from these other pixels to the read circuits. There can also be other transistors present in each pixel, particularly when the pixels are read in voltage and they require the presence of a reinitialisation transistor and a voltage follower transistor, or the sensor also forms an optical sensor in which a transistor is present in each pixel to connect a photodiode from each pixel to a dedicated read circuit.

When a pixel row is heated, there is some undesirable diathermy, i.e. heat transfer between adjacent pixels, in other words heat passes to neighbouring pixels. This generated heat is dissipated in neighbouring pixels and is not used. It is even a nuisance because a waiting time is usually necessary between reading two adjacent pixel rows until heat generated in the adjacent pixel row has been sufficiently dissipated.

Such disadvantages also occur in sensors that read each pixel individually.

PRESENTATION OF THE INVENTION

Thus there is a need to propose a method of capturing a thermal pattern by a sensor with active thermal detection in which heating of pixels when the pixels of the sensor are read is optimised.

To achieve this, one embodiment discloses a method of capturing a thermal pattern by a sensor comprising a matrix of several row and columns of pixels and a plurality of heating elements, each heating element being associated with a pixel or a group of pixels, and each heating element being capable of heating a heat sensitive measurement element of the pixel or of each pixel in the group of pixels independently of the other heating elements during reading of the pixel or of at least one of the pixels in the group of pixels, in which when each pixel called the first pixel in the matrix is read, the heat sensitive measurement element of this first pixel is heated by the heating element associated with this first pixel, and the heat sensitive measurement element of another pixel called the second pixel in the matrix is heated by at least one other heating element associated with this second pixel.

More particularly, during a reading of a first pixel or of a first group of pixels of the matrix, a heating of the heat sensitive measurement element of this first pixel or of each pixel of the first group of pixels by the heating element associated with this first pixel or with this first group of pixels and a heating of the heat sensitive measurement element of another pixel of the matrix, named second pixel, or of a second group of pixels by at least another heating element associated with the second pixel with this second group of pixels are carried out, the second pixel or the second group of pixels being intended to be read before or after the step of reading of the first pixel or of the first group of pixels.

Therefore this method discloses how to transform the defect related to heating interference into an advantage. When one or several pixels are read, instead of heating this or these pixels using only the heating element(s) associated with this or these pixels to be read, at least one other heating element associated with at least one other pixel also heats this other pixel. Thus, when the reading of the first pixel or of the first group of pixels, the heat sensitive measurement element of the first pixel or of each pixel of the first group of pixels and the heat sensitive measurement element of the second pixel or of each pixel of the second group of pixels are heated simultaneously.

The expressions "first pixel" or "first group of pixels", and "second pixel" or "second group of pixels" are used to make a distinction between pixels being read and other pixels that are also heated during the reading.

When the second pixel, or the second group of pixels, is adjacent to the first pixel, or to the first group of pixels, heat generated by heating this second pixel or second group of pixels also contributes to heating the first pixel or the first group of pixels. Therefore the thermal interference phenomenon, i.e. diathermy, is used judiciously herein to inject more heat into the pixel being read (first pixel) and thus obtain a stronger read signal output by the pixel being read.

Two pixels are adjacent to each other when these two pixels are located side by side without any other pixel being positioned between these two adjacent pixels. Similarly, two pixel rows are adjacent to each other when these two pixel rows are located side by side without any other pixel row being positioned between these two adjacent pixel rows. Finally, two heating elements are adjacent to each other when these two heating elements are side by side.

This method is advantageous because for example, it can overcome a limitation on heating imposed by the maximum heating current that can be passed through the heating elements because the total heat received by the pyroelectric capacitors in the pixel row being read can be increased by passing a heating current in one or several adjacent rows of heating elements in addition to that associated with the pixel row being read. The heating current that can be passed in each of the rows of heating elements can be limited for various reasons, for example because:

the current density would otherwise be too high and this can reduce the reliability of the circuit, or even melting or destruction of the circuit, the dimensions of the rows of heating elements are limited so that other rows and/or other signals can be carried, the thickness of the rows of heating element is low due to various manufacturing constraints, the material used to form heating elements can only carry a low current density.

When this second pixel or second group of pixels is not adjacent to the first pixel or first group of pixels but is adjacent to a third pixel or third group of pixels that will be read after the first pixel or first group of pixels, the heat generated by heating this second pixel or second group of pixels preheats this second pixel or second group of pixels that will be neighbour to the third pixel or third group of pixels read later. Thus, when the third pixel of third group of pixels is read, diathermy between the second and third pixels or groups of pixels is reduced or even eliminated because it is possible for the temperatures of the second and third pixels or groups of pixels to be close or similar when the third pixel or third group of pixels is read.

This method is particularly applicable to a sensor in which the heat sensitive measurement elements correspond to pyroelectric capacitors formed by portions of pyroelectric material each located between an upper electrode and a lower electrode.

This method is advantageously applicable to a sensor in which the heat sensitive measurement instruments are heated by the Joule effect by heating elements that comprise electrically conducting portions carrying an electric heating current.

The pixels in a particular row may be read simultaneously, each heating element possibly being associated with a pixel row and comprising an electrically conducting portion capable of heating the heat sensitive measurement element of each pixel in the pixel row. This configuration corresponds to the case of a sensor in which pixel rows are read sequentially. In this case, the first and the second pixels belong to distinct pixel rows.

In this case, the electrically conducting portion of each heating element may be positioned facing the heat sensitive measurement elements of the pixel row with which this heating element is associated. In one advantageous configuration, the electrically conducting portions forming the heating elements may also form the upper electrodes of the pyroelectric capacitors of the sensor pixels, in other words the electrodes closest to the surface of the sensor on which the element for which the thermal pattern is being measured is located.

A group of pixels may correspond to a row of pixels.

In this configuration, reading of a first pixel row may include the use of heating of the heat sensitive measurement elements of this first pixel row by the heating element associated with this first pixel row and by at least one or two other heating elements each associated with a second pixel row adjacent to the first pixel row. In this case, the rows of heating elements associated with pixel rows adjacent to the pixel row being read are used for lateral heating of the pixel row being read and thus increasing the quantity of heat received by the pixels in the row being read. A single other heating element can contribute to heating the pixel row being read particularly when the pixel row being read corresponds to the first or the last pixel row in the matrix because these first and last pixel rows in the matrix only have one neighbouring pixel row. When reading other pixel rows, two other heating elements associated with the two neighbouring pixel rows can contribute to heating this pixel row being read.

In one particular embodiment, heating applied by the other heating element(s) may be used such that a heating power dissipated by this or these other heating elements may be different, for example lower than the heating power dissipated by the heating element associated with the first pixel row. In this case, heat can be provided principally by the heating element associated with the pixel row being read and not by lateral heating provided by the other heating elements.

This control of heat input to the pixel row limits undesirable effects related to diathermy. Heat exchange between two elements depends on thermal conductivities, and especially the temperature difference between these elements. Therefore by heating neighbouring pixel rows, the difference in temperatures between these neighbouring pixel rows and the first pixel row is reduced, which also reduces heat exchanges between these pixel rows. Therefore the heating power injected into the first pixel row dissipates less into neighbouring pixel rows. On the other hand, this lateral heating increases consumption. Therefore a compromise can be made between applying more or less heating to pixel rows adjacent to the pixel row being read.

As a variant, each pixel row may be located between a first heating element associated with this pixel row and a second heating element adjacent to the first heating element, or the heat sensitive measurement elements of each pixel row may be at least partially located facing a first heating element associated with this pixel row and a second heating element adjacent to the first heating element. Furthermore, reading of each pixel row may include heating of the heat sensitive measurement elements of this pixel row by the first heating element associated with this pixel row and by the second heating element adjacent to the first heating element.

In this case, reading of each pixel row may also include the heating of the heat sensitive measurement elements in this pixel row by at least one third heating element adjacent to the second heating element and such that the second heating element is located between the first and third heating elements. Thus, one or several heating elements other than the first and second heating elements can contribute to heating of the pixel row being read.

Heating applied by the second heating element, or by the second and the third heating elements may be applied such that a heating power dissipated by the second heating element or by the second and third heating elements is different, for example lower than the heating power dissipated by the first heating element associated with the pixel row. In this case, heat is provided mainly by heating elements between which the pixel row being read is located or by heating elements facing the pixel row being read, and not by lateral heating applied by other heating elements. This control of heat input to the pixel row limits undesirable effects related to diathermy.

The dissipated heating power depends particularly on the characteristics of the electrically conducting portions of heating elements and the heating currents used. For example, considering the first and second heating elements comprising similar electrically conduction portions, a heating power dissipated by the first heating element that is less than the heating power dissipated by the second heating element can be obtained by circulating a lower heating current in the first heating element than the current circulating in the second heating element.

During a sequence of successive reads of several pixel rows, two rows of successively read pixels may be adjacent or may be separated from each other by at least one other pixel row. When successively read pixel rows are adjacent, there can be a time for cooling of the pixel row being read separating two successive reads of pixel rows. On the other hand, if pixel rows read successively are at a distance from each other, it is possible to read two pixel rows successively without have to wait for a cooling time between the two reads because reading of the next row is not affected by the heating applied during reading of the previous row.

Pixels may be read individually one by one, and reading of the first pixel may include heating of the heat sensitive measurement element of this first pixel by the heating element associated with this first pixel and by at least two, or four, other heating elements associated with at least two, or four, second pixels adjacent to the first pixel. The four second pixels may be distributed regularly around the first pixel. The two or four second pixels may advantageously be pixels neighbouring the first pixel and that are located in the same pixel row or the same pixel column. Other neighbouring pixels can also contribute to heating of the first pixel when it is being read.

The invention also relates to a thermal pattern sensor comprising a matrix of several pixel rows and columns and a plurality of heating elements, each heating element being associated with a pixel or a group of pixels, and each heating element being capable of heating a heat sensitive measurement element of the pixel or of each pixel in the group of pixels independently of the other heating elements during reading of the pixel or at least one of the pixels in the group of pixels, and also comprising a control circuit capable of controlling switching the heating elements on and off and making use of a method of capturing a thermal pattern according to one of the previous claims.

BRIEF DESCRIPTION OF THE DRAWINGS

This invention will be better understood after reading the description of example embodiments given purely for information and that are in no way limitative with reference to the appended drawings on which.

Identical, similar or equivalent parts of the different figures described below have the same numeric references to facilitate comparison between the different figures.

The different parts shown on the figures are not necessarily all at the same scale, to make the figures more easily understandable.

It must be understood that the different possibilities (variants and embodiments) are not mutually exclusive and that they can be combined with each other.

DETAILED PRESENTATION OF PARTICULAR EMBODIMENTS

Figure 1:
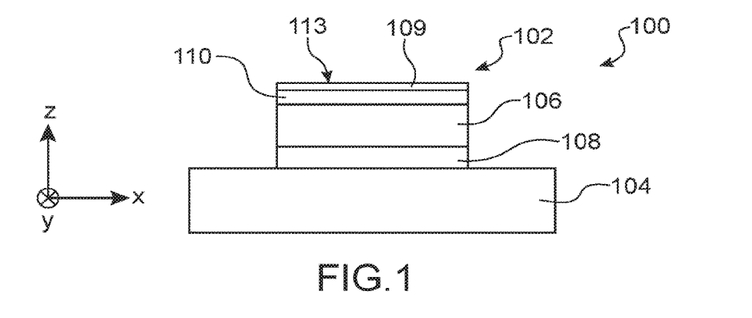
FIG. 1 shows a sectional view of a pyroelectric capacitor of a thermal pattern sensor.

Refer firstly to FIG. 1 that shows a sectional view of a pyroelectric capacitor of a pixel 102, that forms the heat sensitive measurement element of the pixel 102, of a thermal pattern sensor 100.

The sensor 100 comprises a substrate 104 corresponding for example to a glass substrate or a semiconducting substrate (for example silicon). A glass substrate 104 may be used when the sensor 100 is made with TFT transistors, while a semiconductor substrate 104 for example comprising silicon may be used when the sensor 100 comprises transistors made using the MOS technology. The substrate 104 may also be a flexible substrate, for example based on polyimide or PEN (polyethylene naphthalate) or PET (polyethylene terephthalate), on which electronic elements of the sensor 100, such as TFT transistors, are made using the printed electronics technology (for example manufacturing using inkjet type writing heads) or by lithography.

The pixels 102 in the sensor 100 are made by forming a matrix composed of several pixel rows and several pixel columns 102. The pitch of the pixels 102 in the (X,Y) plane (in other words the plane of the substrate 104) may for example be between about 25 μm and 100 μm. In the case of a sensor 100 with resolution equal to 500 dpi ("dots per inch"), the pitch of the pixels 102 is equal to 50.8 μm.

Each pixel 102 in the sensor 100 comprises heat sensitive measurement or detection means formed by a pyroelectric capacitor. Each pyroelectric capacitor comprises a portion 106 of pyroelectric material located between a lower electrode 108 and an upper electrode 110. The pyroelectric material of the portion 106 is advantageously P(VDF-TrFE) or PVDF. As a variant, the pyroelectric material of the portion 106 may be AlN or PZT, or any other pyroelectric material adapted to form a pyroelectric capacitor. The thickness of the portion 106 may for example be between about 500 nm and 10 nm.

Each of the electrodes 108, 110 comprises at least one electrically conducting material, for example a metallic material such as titanium with a thickness equal to about 0.2 μm, and/or molybdenum and/or aluminium and/or a conducting oxide such as ITO (indium and tin oxide) and/or a conducting polymer. One of the electrodes 108, 110, advantageously the upper electrode 110, or each of the two electrodes 108, 110, may comprise of a stack of several electrically conducting materials, for example a Ti/TiN/AlCu stack. The thickness of the each of the electrodes 108, 110 may for example be between about 0.1 μm and 1 μm. The thickness of each of the electrodes 108, 110 may be higher, for example up to about 5 μm, particularly when these electrodes are made by printing using materials such as silver, copper, carbon or PEDOT (poly(3,4-ethylenedioxythiophene).

A protection layer 109, for example corresponding to a layer of aluminium nitride or any other material suitable for creation of this layer, covers the top electrode 110. The thickness of the protection layer 109 may be between a few microns and about 100 μm, or much more (for example of the order of 300 μm or more). A top face 113 of the protection layer 109 corresponds to the surface on top of which there is the thermal pattern to be detected, for example a finger for which the fingerprint is to be detected.

An electric field of about 100 volts per micron of thickness of PVDF is applied once for the entire lifetime of the pyroelectric capacitor on the PVDF in portion 106, so that the PVDF in portion 106 can acquire its pyroelectric (and also piezoelectric) properties. Molecules inside the PVDF are oriented and remain oriented, even when this electric field is no longer applied to the PVDF. The PVDF may thus be polarised by applying an initial polarisation voltage to the terminals of the electrodes 108, 110.

After this initial polarisation, when a temperature variation ΔT is applied to the portion 106, this temperature variation ΔT causes the development of an additional electric field generating charges ΔQ between the electrodes 108, 110 such that:

$$\Delta Q = S \cdot \gamma \cdot \Delta T$$

The parameter S corresponds to the surface area of the portion 106 facing each of the electrodes 108, 110. The parameter γ corresponds to the pyroelectric coefficient of the pyroelectric material of the portion 106. For example, the pyroelectric coefficient γ of PVFD-TrFE is equal to about 32 μC/m²/K.

Since the portion 106 and the electrodes 108, 110 forming a capacitor with value C to which parasite capacitances Cp are added, the generated charges ΔQ induce a difference of electrical potentials ΔV between the electrodes 108, 110 such that:

$$(C+C_p)\Delta V = \Delta Q = S \cdot \gamma \cdot \Delta T$$

In addition to the charges generated by the capacitor with value C, other parasite charges may also be generated through parasite capacitances present, for example those related to the gate of the read transistor in the case of a voltage read circuit.

When the potential on the read electrode (composed of one of the electrodes 108, 110) is fixed ("current" read), the generated charges flow to the read circuit forming an integrated current at the output, in this case with:

$$\frac{\Delta Q}{\zeta} = \frac{S \cdot \gamma \cdot \Delta T}{\zeta}$$

in which ζ corresponds to the integration time during which the pixel makes the measurement. The advantage of current reading is that it is insensitive (as a first order of magnitude) to the value of the capacitances, and particular parasite capacitances.

The sign of the electrical voltage ΔV obtained between electrodes 108, 110, or the direction of the current in the case of current reading, depends on the direction of the electric field used to initially polarise the PVDF of the portion 106. In the case of some other pyroelectric materials such as aluminium nitride, this initial polarisation direction depends on the way in which the pyroelectric material was deposited, its order and its crystallographic orientation. Furthermore, the electrical voltage ΔV obtained, or the current direction, may be positive or negative depending on whether the temperature variation applied to the pyroelectric capacitor is positive or negative.

The sensor 100 also comprises heating elements dissipating a certain quantity of heat in the pixels 102, and more particularly in the portion 106 of pyroelectric material, when reading pixels 102. In the example embodiment described herein, these heating elements are formed directly by one of the electrodes 108, 110 of each of the pyroelectric capacitors. In the example on FIG. 1, the heating element of the pyroelectric capacitor of the pixel 102 is formed by the upper electrode 110. The other electrode of the pyroelectric capacitor, in this case the lower electrode 108, acts as the pixel reading electrode 102.

The portion 106 of pyroelectric material is heated by circulating a current in the electrode that will form the heating element. This electrode is also used to polarise the pyroelectric capacitor. Thus, the heating resistance of each pixel 102 is therefore also used to polarise an electrode of the pyroelectric capacitor formed by the portion 106 and the electrodes 108, 110 of each of pixel 102 during the measurement made by these pixels 102 (the polarisation applied during a measurement is different from the initial polarisation of the PVDF described above).

One of the electrodes 108, 110 of pixels 102 can be used to form the heating elements because the value of the electrical potential applied to this electrode is constant during a read of the thermal pattern.

Figure 2:
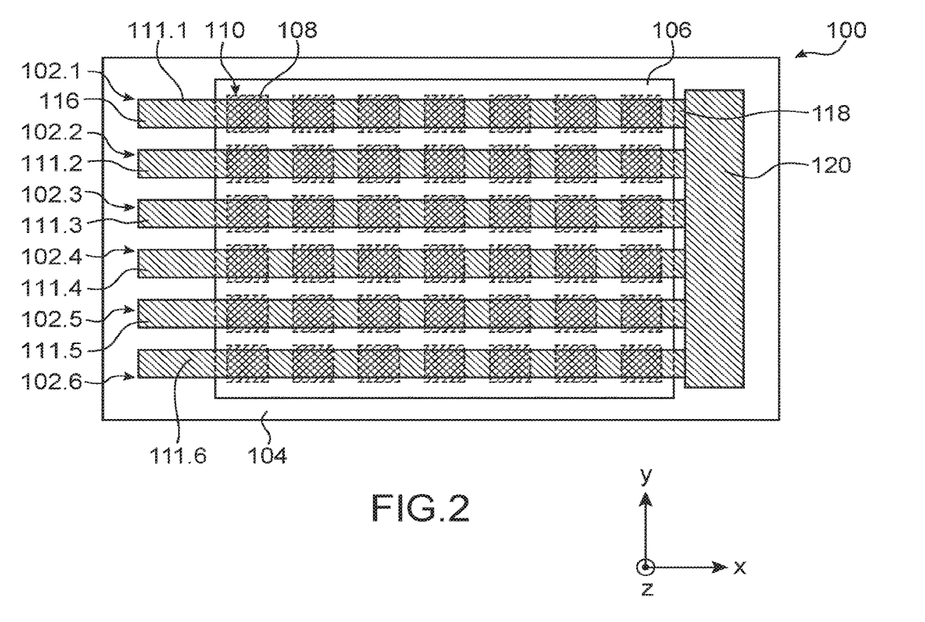
FIGS. 2 to 5 show top views of part of the thermal pattern sensor according to different embodiments.

FIG. 2 shows a top view of several pixels 102 of the sensor 100 according to a first embodiment.

The lower electrodes 108 that correspond to read electrodes of the pixels on which charges generated by the pyroelectric capacitors will be recovered to be read, are formed from distinct first portions of electrically conducting material electrically insulated from each other. The cross-section of each of these first conducting portions in the plane of the substrate 104 ((X, Y) plane) is rectangular and they are located adjacent to each other in the form of a matrix to form the matrix of pixels 102.

The pyroelectric material is made in the form of a single portion 106, or a single layer 106 covering all the lower electrodes 108.

The upper electrodes 110 of the pixels are formed from several second portions of conducting material 111, references 111.1 to 111.6 on FIG. 2, each forming the upper electrodes 110 of pixels 102 located on the same row. Each of the second portions 111 comprises a first end 116 to which a heating potential is applied, and a second end 118 connected to another conducting portion 120 common to all second portions 111 and connected to the ground. Electrical potentials applied to the first ends 116 of the second portions 111 are similar in each of the portions 111.

Thus, each of the second portions 111 forms a heating element capable of heating the pixel row 102.$i$, where i is an integer number between 1 and n (for a sensor 100 comprising n pixel rows).

A control circuit (not shown on FIG. 2) capable of controlling switching the heating elements of the sensor 100 on and off may for example comprise an electrical connection applying an existing voltage in the sensor 100 on the end 116 of each of the second portions 111. For example, if the end 118 is connected to the ground and a heating potential $V_{heating}$ is applied to the end 116, a current then flows from end 116 to end 118 of the second portion 111, causing heating in the second portion 111 by the Joule effect, and thus heating the portion 106 of the pixels 102 in the pixel row heated by this second portion 111. The value of the heating voltage is chosen as a function of the required heating power, this power depending particularly on the thickness of the portion 106 to be heated and the thickness of the protection layer 109, the pyroelectric coefficient of the material of portions 106, the sensitivity of the read circuit, the degree of noise in the read circuit and the integration time. For example, the heating power in a pixel 102 may be between about 0.1 mW and 10 mW.

Advantageously, the second portions of conducting material 111 acting as a heating resistance for the pixels 102 also form the upper electrodes 110 of the pixels 102 that are located above the pyroelectric material and not the lower electrodes 108 because this arrangement makes it possible to connect conducting portions of the pyroelectric capacitors closest to the exterior of the sensor 100 to the ground of the sensor 100. Such an arrangement provides protection against electrostatic discharges (ESD) because if such a discharge occurs, there will then be a preferred path in which electrical charges due to this discharge can flow, which limits voltage breakdowns with fragile active elements of the sensor 100 such as transistors.

However, the heating elements may be located under the portion of pyroelectric material 106 and form the lower electrodes 108.

Each pixel row 102 may be heated independently of all the others. Values of heating voltages applied to the second portions 111 are adjusted relative to the resistivity of the metal in the second portions 111 so as to generate the required thermal energy and thus dissipate the required heating power in the pixels 102. For example, a sensor 100 with a matrix of 400×300 pixels at 500 dpi is considered (corresponding to pixels 102 located adjacent to each other at a pitch of 50.8 µm). For such a sensor 100, when the second portions 111 contain titanium, each being about 200 nm thick with a resistivity of the order of 2 ohms per square, each of the second portions 111 forming upper electrodes 110 of a row of 400 pixels each with a width (dimension along the y axis on FIG. 4, in other words the dimension located in the plane in which the principal surface of the second portion 111 lies and that is perpendicular to the principal dimension, in other words the length, of the second portion 111) equal to about 40 µm has a resistivity equal to 400×50/40=500 squares, giving 1 kOhm. The electrical potential applied to obtain a dissipated power per pixel 102 equal to about 0.1 mW, or about 40 mW for each pixel row 102, is about 6.3 volts applied on each of the ends 116 of the second portions 111. The electrical potential applied to obtain a dissipated power of about 1 mW per pixel is about 20 V, applied to each end 116 of the second portions 111.

Thus, the required energy in each row may be chosen by modulating the value of the voltage or current applied on the row.

In the example embodiment shown on FIG. 2, the second portions 111 form conducting strips with a uniform width each extending along a pixel row 102. Heat is thus diffused uniformly along each conducting strip.

When a pixel row is being read, the electrical potential $V_{heating}$ applied on one of the electrodes of the pyroelectric capacitor is constant throughout the reading time of a pixel. On the other hand, since the second portion of conducting material 111 to which this potential is applied is common to several pixels 102, the value of the heating potential applied to one of the electrodes of the pyroelectric capacitors of each of these pixels 102 is different on each of the different pixels. Considering one pixel row of the sensor 100 shown on FIG. 2, a potential equal to approximately $V_{heating}$ is applied to the upper electrode 110 of the pyroelectric capacitor closest to the end 116. An electrical potential equal to approximately $V_{heating}-\delta V$ is applied to the upper electrode 110 of the next pyroelectric capacitor. The values of electrical potentials applied on the upper electrodes 110 of the pyroelectric capacitors reduce in proportion to their distance from the end 116. When the conducting portion 120 is connected to the ground, an electric potential equal to approximately 0V, in other words the electrical potential of the ground, is applied to the upper electrode 110 of the last pyroelectric capacitor corresponding to that neighbouring the conducting portion 120. This variation of the electric heating potential applied from one pixel to the next does not modify the heating applied from one pixel to the next because the current flowing in the second conducting portion 111 causing heating is the same in the entire second conducting portion 111 and the same for all pixels 102 because the heating resistances 128 are identical for all pixels 102.

When reading the pixels of the row being read, the values of potentials on each electrode are different from each other. On the other hand, the difference in voltages or the difference in the number of charges generated at the terminals of the pyroelectric capacitors for the same temperature variation, is identical. The reading made is of the excess charge generated relative to the reference voltage, that may be positive or negative.

When one of the pixel rows is being read, the sensor 100 heats the row of heating elements above the pixel row being read, and also heats one or several rows of heating elements associated with the immediately adjacent pixel rows, in order to improve heating of pixel rows. Thus, on the example in FIG. 2, when the second pixel row 102.2 is being read, heating voltages are applied to the terminals of the second portion 111.2 that is associated with the second pixel row 102.2 and to the terminals of the second portions 111.1 and 111.3 that are associated with the two pixel rows 102.1 and 102.3 immediately adjacent to the pixel row 102.1 being read. According to another example, when the fourth pixel row 102.4 is being read, heating voltages are applied to the terminals of the second portions 111.3, 111.4 and 111.5.

For the first pixel row 102.1 and the last pixel row 102.6 that only comprises one adjacent pixel row, only the row of heating elements associated with this single row of adjacent pixels is heated in addition to that associated with the pixel row being read. Thus, when the first pixel row 102.1 is read, heating voltages are applied to the terminals of the second portion 111.1 associated with the first pixel row 102.1 and to the terminals of the second portion 111.2 that is associated with the second pixel row 102.2. Similarly, when reading the last pixel row 102.6, heating voltages are applied to the terminals of the second portion 111.6 that is associated with the last pixel row 102.6 and to the terminals of the second portion 111.5 that is associated with the fifth pixel row 102.5.

As a variant, the sensor 100 may be made such that it comprises a second additional portion 111.0 such that the second portion 111.1 is located between the second portion 111.2 and this second additional portion 111.0 (that is not located above any heat sensitive pixel measurement element). Similarly, the sensor 100 may comprise another second additional portion 111.n+1 such that the second portion 111.n (in the case of a sensor comprising n pixel rows) is located between the second portion 111.n−1 and this other additional second portion 111.n+1 (that is also not located above any heat sensitive pixel measurement element).

The read sequence of pixel rows in the sensor 100 used may be as follows:
 select the pixel row 102.i to be read, for example by putting the pixel selection transistors for row 102.i into the conducting state;
 switch on the heating elements associated with pixel rows 102.i−1, 102.i and 102.i+1 by the application of a heating voltage on each of the second portions 111.i−1, 111.i and 111.i+1 associated with these pixel rows;
 reinitialise read circuits coupled to all pixel columns (this reinitialisation is made after starting to heat pixels so that no undesirable noise is injected into the read circuits at the time that the heating is switched on);
 start integration of pixels in row 102.i;
 wait for the integration time ζ, for example equal to 1 ms;
 read signals received by the read circuits that correspond to temperature variations measured by the pixels of row 102.i that is being read;
 switch heating elements off;
 deselect row 102.i.

The parameter "i" corresponds to an integer number between 1 and n, where n corresponds to the number of pixel rows in the sensor.

In general, the integration time is between about 30 µs and 1 ms so as to obtain a temperature variation between about 0.1 K and 2 K with power injections between about 0.1 and 1 mW per pixel.

Regardless of whether the read is made in charges (or in current) or in voltage, heating is preferably not switched on and off during the integration time and the during reading. Indeed, switching the heating on generates an important variation in the potential of one of the electrodes of the pyroelectric capacitors of the pixels read. Therefore this variation is repeated on the other electrode of the pyroelectric capacitors of the pixels being read. For some pixels, this variation in the potential is much larger than the signal that will be read by these pixels. For the same reason, all parasites on the potential $V_{heating}$ should be minimised during the integration time, particularly parasites related to the current demand due to the operation of other electronic parts of the sensor 100.

After reading pixel row 102.i of the sensor 100, cooling takes place during a certain period before the next pixel row 102.i+1 is read. This cooling time is for example between about 3 and 5 times the heating time of the pixel row 102.i that has just been read.

Therefore the pixels 102 of the sensor 100 may be read in sequence starting from a first pixel row 102.1, for example the row at the top of the sensor 100, and terminating by the last pixel row 102.n, for example the row at the bottom of the sensor 100, respecting a certain cooling time between reading two adjacent pixel rows.

As a variant, pixel rows separated from each other by one or several other pixel rows may be read successively, rather than reading adjacent pixel rows in sequence (in other words row 102.i, then row 102.i+1, then row 102.i+2, etc.). Thus, two pixel rows separated from each other by at least 2, 3 or 4 or more pixel rows may be read consecutively. For example, the following pixel rows can be read in sequence (the numbers represent the order of pixel rows, with row 102.1 corresponding to the pixel row at the top of the sensor 100 and row 102.n being the pixel row at the bottom of the sensor 100): 1, 5, 10, 15, etc., then 2, 6, 11, 16, etc. Thus, by choosing a read sequence with pixel rows at a distance from each other, there is no need to wait for the previously read pixel row to cool before reading the next pixel row because heat remaining from the pixel row that has just been read has no impact on the next pixel row that will be read, since the next row is not adjacent to the pixel row that has just been read.

Furthermore, according to one variant (that can be applied when pixel rows read consecutively are or are not adjacent), when reading the pixel row 102.i, it is possible that one or several other rows of heating elements are switched on in addition to the heating supplied by heating elements associated with the directly adjacent pixel rows (in other words pixel rows 102.i−1 and 102.i+1). For example, heating elements associated with pixel rows 102.i−2, 102.i−1, 102.i, 102.i+1 and 102.i+2, or even a larger number of rows of heating elements, may all be switched on when reading pixel row 102.i.

The sensor 100 shown on FIG. 2 is only one example embodiment of a thermal pattern sensor to which the method described above, in which heating elements associated with pixel rows adjacent to the pixel row being read are switched on when this pixel row is read, can be applied.

Figure 3:
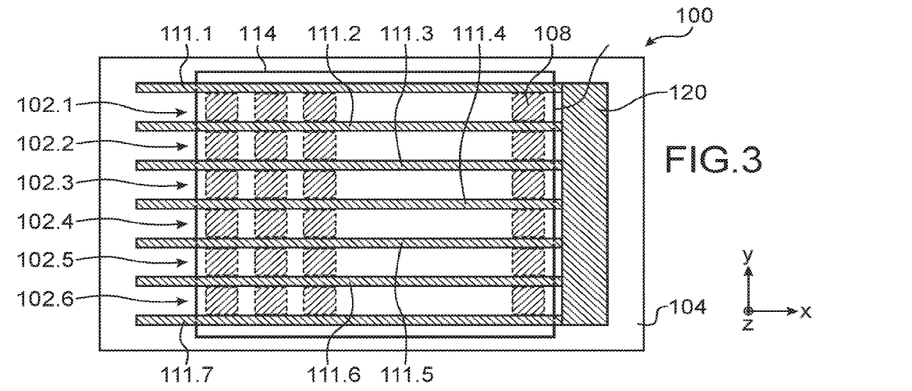

FIG. 3 shows another embodiment of a thermal pattern sensor 100 to which this read method can be applied.

Unlike the sensor 100 shown on FIG. 2 in which each of the second portions 111 forms heating elements and upper electrodes 110 of the pixels, the sensor 100 shown on FIG. 3 comprises heating elements formed by the second portions 111 that are not facing the lower electrodes 108 and therefore heat sensitive pixel measurement elements. Thus, the upper electrodes of the pixels 102 of this sensor 100 are formed from an electrically conducting layer 114 located on the pyroelectric material. This electrically conducting layer 114 is covered by a dielectric layer on which the second portions 111 are placed. This electrically conducting layer 114, that for example includes an electrically conducting ink, thus forms electromagnetic shielding between the element for which the thermal pattern is to be detected, for example a finger in the case of a fingerprint sensor 100, and portions 111 forming heating elements of pixels 102, thus preventing electromagnetic noise (for example noise at 50 Hz originating from the grid) being recovered in the measurements made. In this configuration, the heating elements are arranged as close as possible to the element for which the thermal pattern is detected by the sensor 100.

Thus, in the example on FIG. 3 on which six pixel rows 102.1 to 102.6 are shown, each of these pixel rows (more precisely each row of upper electrodes of these pixel rows) is located between two second portions 111. Considering a sensor 100 comprising n pixel rows, each pixel row 102.$i$ is located between two second portions 111.$i$ and 111.$i$+1, in other words between a first heating element associated with this pixel row and a second heating element adjacent to the first heating element.

When each of the pixel rows is being read, at least the heating elements formed by the two second portions 111 between which each of the pixel rows 102 is located are switched on to heat the pixel row. Thus, a heating voltage is applied to the ends of each portion 111.3 and 111.4 (or 111.$i$ and 111.$i$+1), to read the pixel row 102.3 (or more generally 102.$i$).

A larger number of heating elements may be switched on when reading a pixel row of the sensor 100 shown on FIG. 3. For example, when reading the pixel row 102.3 (or more generally 102.$i$), a heating voltage may be applied to the ends of each of the portions 111.3 and 111.4 (or 111.$i$ and 111.$i$+1), but also to the ends of at least one of the portions 111.2 and 111.5 (or 111.$i$−1 and 111.$i$+2), or even a larger number of portions 111.

In the example on FIG. 3, the rows of heating elements, in other words the second portions 111, are located between the pixel rows. According to another example embodiment of the sensor as shown on FIG. 4, the second portions 111 may be made such that each of these second portions 111 partially covers two adjacent pixel rows. Thus, in the example on FIG. 4, the portion 111.2 partially covers each of the pixel rows 102.1 and 102.2. In general, each pixel row 102.$i$ is covered by the second portions 111.$i$ and 111.$i$+1. Each of the second portions 111.1 and 111.$n$ (corresponding to the portion 111.7 on FIG. 4) covers part of a single pixel row.

Figure 4:
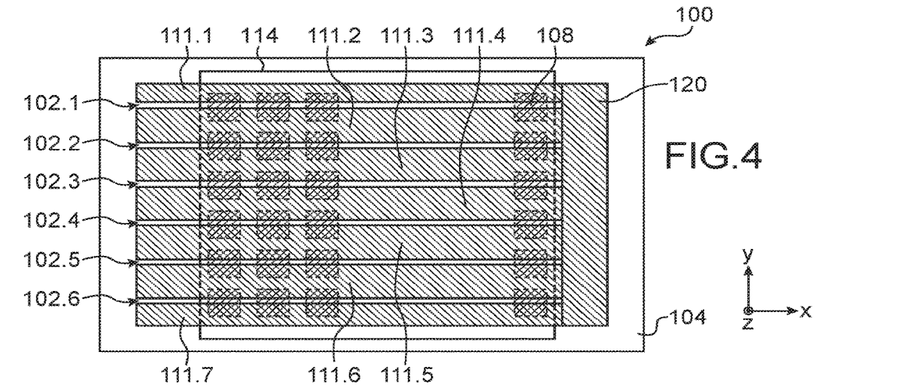

When each of the pixel rows is being read, at least the heating elements formed by the two second portions 111 covering the pixel row being read are switched on to heat this pixel row. Thus, a heating voltage is applied to the ends of each portion 111.3 and 111.4 (or 111.$i$ and 111.$i$+1), to read the pixel row 102.3 (or more generally 102.1).

A larger number of heating elements may be switched on when reading a pixel row of the sensor 100 shown on FIG. 4. For example, when reading the pixel row 102.3 (or more generally 102.$i$), a heating voltage may be applied to the ends of each of the portions 111.3 and 111.4 (or 111.$i$ and 111.$i$+1), but also to the ends of at least one of the portions 111.2 and 111.5 (or 111.$i$−1 and 111.$i$+2), or even a larger number of rows of heating elements.

The example embodiment shown on FIG. 4 is more advantageous than the embodiment shown on FIG. 3 because part of each of the heating elements is located above the pixels and not only at the side of the pixels as is the case on the example embodiment in FIG. 3. Heat generated by the heating elements is thus better transmitted to the heat sensitive measurement elements of the pixels.

In the example embodiment on FIG. 4, the coverage of each pixel row 102 by the second portions 111 is approximately symmetrical about the principal axis of the pixel rows, in other words the areas of the pixel rows 102 facing each of the second portions 111 are approximately equal to each other.

Figure 5:
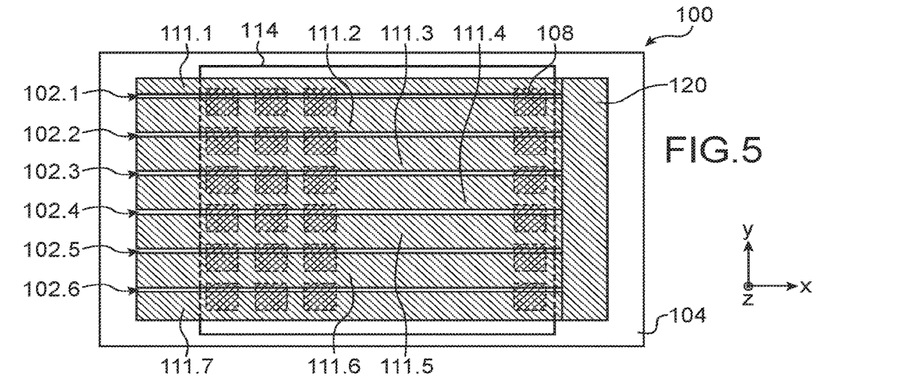

As a variant, the pixel rows 102 may be covered by dissymmetric portions 111, as in the example embodiment shown on FIG. 5. On this variant, the surface areas of the pixel row 102.$i$ facing each of the two second portions 111.$i$ and 111.$i$+1 are not equal to each other and for example are such that the surface area facing the second portion 111.$i$+1 is larger than that facing the portion 111.$i$.

For reasons of clarity in FIGS. 3, 4 and 5, the portion 106 of pyroelectric equipment cannot be seen on FIGS. 3, 4 and 5.

In the embodiments described above, when each of the pixel rows is being read, several heating elements are switched on and the same heating current is passed in each of the heating elements so that these elements will dissipate the same heating power.

Advantageously, the sensor control circuit 100 modulates the current injected into the heating elements. For example, considering the sensor 100 described above with reference to FIG. 2 when the pixel row 102.$i$ is being read, a heating current with an intensity equal to $I_{heating}$ may be injected into the portion 111.$i$ and a heating current with an intensity equal to $I_{heating}/2$ may be injected into the adjacent portions 111.$i$−1 and 111.$i$+1. This can control the injection of heat, optimise consumption of electricity to obtain a maximum variation of the pixel temperature relative to undesirable diathermy effects since heat is concentrated at the pixel row being read, and the temperature at the sides of the row is minimal.

In general, when reading a pixel row, heating currents may be injected into a larger number of adjacent heating elements, these heating currents having different intensities depending on their distance from the pixel row being read. The profile of the curve formed by these heating currents injected into the heating elements may correspond approximately to the profile of a Gaussian curve centred on the heating element associated with the pixel row being read, in other words such that the highest heating power is dissipated by the heating element associated with the pixel row being read, and the heating power dissipated by other heating elements reduces as a function of their distance from the pixel row being read. For example, when reading a pixel row 102.$i$, it is possible to inject a heating current with intensity equal to $I_{heating}$ into portion 111.$i$, to inject a heating current with intensity equal to $I_{heating}/3$ into adjacent portions 111.$i$−1 and 111.$i$+1, to inject a heating current with intensity equal to $I_{heating}/8$ into portions 111.$i$−2 and 111.$i$+2, and even to inject a heating current with intensity equal to $I_{heating}/16$ into portions 111.$i$−3 and 111.$i$+3. Such a profile of injected heating currents may or may not be symmetric about the heating element associated with the pixel row being read.

Different profiles of heating currents injected into the heating elements may be envisaged depending on the position of the pixel row being read within the sensor.

It is also possible that the different heating elements used to read a pixel row are not switched on simultaneously, but that there is a delay between them. For example, in the case in which the heating elements 111.$i$−1, 111.$i$ and 111.$i$+1 are switched on when pixel row 102.$i$ is being read, it is possible to switch heating element 111.$i$ on first, and then for example to switch heating elements 111.$i$−1 and 111.$i$+1 on 100 microseconds later.

According to another variant, the heating currents injected into the different heating elements may be adapted as a function of the heating level applied previously, if any, for one or several of these different rows of heating elements during a previous read of a pixel row. For example, considering that the heating elements 111.*i*−1, 111.*i* and 111.*i*+1 were switched on when reading pixel row 102.*i*, when reading the next pixel row 102.*i*+1, it is possible to inject a heating current C1 in heating element 111.*i*+2, a heating current C2 in heating element 111.*i*+1, and a heating current C3 in heating element 111.*i*, such that C1>C2>C3. Given that the heating element 111.*i*+2 was not used during the previous read of a pixel row, a higher power has to be injected into this heating element than the powers injected into heating elements 111.*i* and 111.*i*+1. Furthermore, since the heating element 111.*i* was used to read the two previous pixel rows, it is already warm and therefore requires a lower heating power than that used for the heating element 111.*i*+1 that was used only for reading the previous pixel row. In this case, integration of pixels to be read has already started.

A pixel row 102.1 may also be read in two phases: a first phase during which only one heating element 111.*i* associated with this pixels row receives a heating current, then a second phase during which the heating element 111.*i* and one or several other adjacent heating elements receive a heating current. Post-processing of the measurement signals obtained during these two measurement phases can extract useful information and separate everything related to the pixel row 102.*i* and reinforce the signal, from everything related more particularly to adjacent pixel rows.

These variants in which not all injected heating currents are the same and/or in which the heating elements are not switched on simultaneously may be applied to all the previously described sensors 100.

In the various embodiments described above, the heating elements that have been powered up in parallel to the heating element associated with the pixels row being read correspond to heating elements adjacent to that associated with the pixels row. As a variant, the heating elements switched on in parallel to the heating element associated with the pixel row being read may correspond to those associated with pixel rows adjacent to the pixel row that will be read later. For example, considering that the pixel row 102.*i* is read in a first step, and then pixel row 102.*i*+5 is read in a second step, and then pixel row 102.*i*+10 is read in a third step, it is possible to switch the heating element 111.*i* and heating elements 111.*i*+4 and 111.*i*+6 on during reading of the pixel row 102.*i*. Thus when pixel row 102.*i*+5 is read, the adjacent heating elements had already been heated and are therefore thermally stable because they are in the process of cooling. When pixel row 102.*i*+5 is read, the heating element 111.5 and heating elements 111.9 and 111.11 are heated so these heating elements are already warm the next time the pixels row 102.10 is read.

In the embodiments and variants described above, the sensor 100 comprises pixel rows and heating elements, each of which applies collective heating to all pixels in the same row. However, the sensor 100 may comprise heating elements capable of heating pixels individually, these heating elements then being controllable individually and independently from the others. In such a sensor, pixels are read pixel by pixel, and not pixel row by pixel row. In this case, the principles presented above for the heating of heating elements around the pixel row being read are applicable to the individual pixels of this sensor. For example, considering reading of pixels 102.(*i,j*), in other words the pixel in row i and column j of sensor 100, in addition to switching on the heating element associated with pixel 102.(*i,j*) during this read, one or several heating elements associated with pixels located around pixel 102.(*i,j*), for example heating elements associated with pixels 102.(*i*−1,*j*), 102.(*i,j*−1), 102.(*i, j*+1) and 102.(*i*+1,*j*), possibly also even heating elements associated with pixels 102.(*i*−1,*j*−1), 102.(*i*−1, *j*+1), 102.(*i*+1,*j*−1), and 102.(*i*+1, *j*+1) or other heating elements further from the pixel being read, are also switched on.

The different variants described above are also applicable to such a sensor.

In the example embodiments of sensor 100 described above, the heating elements are formed from the same electrically conducting level as that used to form the upper electrodes of pyroelectric capacitors of pixels. As a variant, it is possible that the heating elements are not formed from this electrically conducting level, but from another electrically conducting level. Thus, the variant by which the upper electrodes are formed by an electrically conducting layer distinct from the heating elements may be applied to all embodiments described herein.

According to another variant, an electromagnetic shielding layer of the sensor may be formed by placing a dielectric layer on the heating elements 111, and placing an electrically conducting layer connected to a reference potential, on this dielectric layer.

Although not shown, the sensor 100 comprises a control circuit to apply the control signals described above to control reading of the pixels 102.

The thermal pattern detected by the sensor 100 advantageously represents a fingerprint.

Although not shown, the sensor 100 may also comprise an electronic processing circuit capable of creating a global image of the thermal pattern starting from measurements made at each pixel 102. This electronic processing circuit may also compare this image with several images stored in a database so as to identify whether or not the detected thermal pattern corresponds to one of the images stored in the database. The electronic processing circuit may also display an image of the detected thermal pattern.

The invention claimed is:

1. A method of capturing a thermal pattern by a sensor comprising a matrix of several rows and columns of pixels and a plurality of heating elements, each heating element being associated with a pixel a group of pixels, and each heating element being configured to heat a heat sensitive measurement element for measurement of the pixel or each pixel in the group of pixels independently of the other heating elements during reading of the pixel or of at least one of the pixels in the group of pixels, the method comprising:

during a reading of a first pixel or of a first group of pixels, the heat sensitive measurement element of the first pixel or of each pixel of the first group of pixels is heated by a heating element associated with the first pixel or with the first group of pixels, and also during the reading of the first pixel or of the first group of pixels, the heat sensitive measurement element of a second pixel, or of a second group of pixels, in the matrix is heated by at least one other heating element associated with the second pixel or with the second group of pixels, the second pixel or the second group of pixels being read before or after the reading of the first pixel or of the first group of pixels.

2. The method according to claim 1, wherein the second pixel is adjacent to the first pixel or to a third pixel that will be read after the first pixel.

3. The method according to claim 1, wherein pixels in a particular row of said several rows are read simultaneously, each heating element being associated with a row of pixels and comprising an electrically conducting portion configured to heat the heat sensitive measurement element of each pixel in the particular row.

4. The method according to claim 3, wherein the electrically conducting portion of said each heating element is positioned facing the heat sensitive measurement elements of the particular row with which this heating element is associated.

5. The method according to claim 4, wherein reading of a first row of pixels includes the use of heating of heat sensitive measurement elements of the first row of pixels by the heating element associated with the first row of pixels and by at least one or two other heating elements each associated with a second row of pixels adjacent to the first row of pixels.

6. The method according to claim 5, wherein heating applied by at least one other heating element is used such that a heating power dissipated by said at least one other heating element is different from a heating power dissipated by the heating element associated with the first row of pixels.

7. The method according to claim 3, wherein:
each row of pixels of said several rows is located between a first heating element associated with the particular row of said several rows and a second heating element adjacent to the first heating element, or the heat sensitive measurement elements of said each row of said several rows are at least partially located facing a first heating element associated with the particular row of said several rows and a second heating element adjacent to the first heating element, and
reading of said each row of said several rows includes heating of the heat sensitive measurement elements of the particular row of said several rows by the first heating element associated with the particular row of said several rows and by the second heating element adjacent to the first heating element.

8. The method according to claim 7, wherein reading of said each row of said several rows also includes heating of the heat sensitive measurement elements in the particular row of said several rows by at least one third heating element adjacent to the second heating element, and such that the second heating element is located between the first and third heating elements.

9. The method according to claim 7, wherein heating applied by the second heating element, or by the second and the third heating elements, is applied such that a heating power dissipated by the second heating element or by the second and third heating elements is different from a heating power dissipated by the first heating element associated with the particular row.

10. The method according to claim 3, wherein during a sequence of successive reads of several rows of pixels, two rows of successively read pixels are adjacent or separated from each other by at least one other row of pixels.

11. The method according to claim 5, wherein, when a row of pixels is being read, a heating power dissipated by a heating element associated with the row of pixels is higher than a heating power dissipated by a heating element associated with a previously read row of pixels and less than a heating power that will be dissipated by a heating element associated with another row of pixels to be read later.

12. The method according to claim 1, wherein pixels are read individually one by one, and wherein reading of the first pixel includes heating of the heat sensitive measurement element of the first pixel by the heating element associated with the first pixel and by at least two other heating elements associated with at least two second pixels adjacent to the first pixel.

13. A thermal pattern sensor comprising a matrix of several rows and columns of pixels and a plurality of heating elements, each heating element being associated with a pixel or a group of pixels, and each heating element being configured to heat a heat sensitive measurement element for measurement of the pixel or of each pixel in the group of pixels independently of the other heating elements during reading of the pixel or at least one of the pixels in the group of pixels, and also comprising a control circuit configured to control switching the heating elements on and off and using the method of capturing a thermal pattern according to claim 1.

14. A thermal pattern sensor according to claim 13, wherein the heat sensitive measurement element of each pixel includes at least one pyroelectric capacitor formed by at least one portion of pyroelectric material located between a lower electrode and an upper electrode, wherein one of the lower and upper electrodes is a read electrode of the pixel, wherein the heating element associated with each pixel is configured to heat the at least one portion of pyroelectric material of the pyroelectric capacitor of the pixel by the Joule effect during a measurement of the thermal pattern by the pyroelectric capacitor of said pixel and is formed by the other of the lower and upper electrodes.

* * * * *